United States Patent [19]
Shoenhair et al.

[11] Patent Number: 5,339,692
[45] Date of Patent: Aug. 23, 1994

[54] ULTRASONIC RAIL WEB CENTERLINE DETECTOR

[75] Inventors: John J. Shoenhair, New Hope, Minn.; Alex Ivachev, Marysville, Australia

[73] Assignee: Loram Maintenance of Way, Inc., Hamel, Minn.

[21] Appl. No.: 816,958

[22] Filed: Jan. 3, 1992

[51] Int. Cl.5 .......................................... G01N 29/10
[52] U.S. Cl. .................................... 73/636; 73/639
[58] Field of Search ............... 73/636, 634, 620, 625, 73/641, 639

[56] References Cited

U.S. PATENT DOCUMENTS

| | | | |
|---|---|---|---|
| 2,951,365 | 9/1960 | Legrand | 73/67.8 |
| 3,415,110 | 12/1968 | Cowan | 73/67.8 |
| 3,768,306 | 10/1973 | Stearns | 73/67.8 R |
| 3,960,005 | 6/1976 | Vezina | 73/67.7 |
| 4,044,594 | 8/1977 | Owens et al. | 73/636 |
| 4,143,553 | 3/1979 | Martens et al. | 73/625 |
| 4,235,112 | 11/1980 | Kaiser | 73/636 |
| 4,457,178 | 7/1984 | Turbe et al. | 73/636 |
| 4,689,995 | 11/1987 | Turbe | 73/636 |
| 4,862,647 | 9/1989 | Vieau | 51/178 |

FOREIGN PATENT DOCUMENTS

| | | | |
|---|---|---|---|
| 241181 | 12/1960 | Australia | 73/636 |
| 57409/86 | 2/1989 | Australia | G01N 29/04 |
| 33327/89 | 10/1989 | Australia | G01N 29/04 |
| WO85/04484 | 10/1985 | PCT Int'l Appl. | G01N 29/00 |
| WO85/04485 | 10/1985 | PCT Int'l Appl. | G01N 29/04 |

OTHER PUBLICATIONS

"Automatic Control of Ultrasonic Rail-Inspection Transducers", by W. D. Kaiser, Battelle-Columbus Laboratories.
"LN1, New Generation Ultrasonic Rail Flaw Detection Technology in the Palm of Your Hand", Rail Technology International Pty. Ltd.

Primary Examiner—Hezron E. Williams
Assistant Examiner—Nashmiya Ashraf
Attorney, Agent, or Firm—Patterson & Keough

[57] ABSTRACT

An ultrasonic rail web centerline detector locates the web centerline (18) of a longitudinal rail (12) having a head (80), a base (82), and a web therebetween. The detector includes an ultrasound sensor (14) acoustically coupled to the head (80) of the rail (12) for transmitting ultrasound energy through the rail (12) and for generating electrical signals corresponding to received reflected ultrasound energy. A controller (16) responsive to the electrical signals generates control signals representative of a lateral and angular displacement of the ultrasound sensor (14) with respect to the web centerline (18) of the rail. The position of the ultrasound sensor is adjusted as a function of the control signals representative of the lateral and angular displacement. The ultrasound sensor includes a center transceiver (30) and side transceivers (32, 34) which are acoustically coupled to the head (80) of the rail (12). The side transceivers (32, 34) are positioned symmetrically on opposite sides of the center transceiver (30).

6 Claims, 7 Drawing Sheets

ULTRASONIC RAIL WEB CENTERLINE DETECTOR

TECHNICAL FIELD OF THE INVENTION

The present invention pertains generally to the field of rail maintenance equipment, and more particularly to an apparatus for detection of the web centerline of a rail for use in maintenance thereof.

BACKGROUND OF THE INVENTION

Safe and economic railway systems require the performance of periodic rail maintenance. As part of the maintenance, it is prudent that the rails be inspected for faults, that grinding machines maintain the rails in smooth, properly shaped condition to allow safe movement of rail traffic thereon, and that the rail geometry be ascertained to determine whether various rail parameters are within specified acceptable tolerances, or whether the rails should be condemned. To perform certain of these maintenance procedures, it is helpful to determine where the centerline of the web of the rail is located. In this regard, the web centerline is utilized as a reference point to properly grind the rail, to determine if flaws are at unsafe locations within the rail, etc.

Numerous approaches to detect rail web centerline have been proposed. For example, laser triangulation measurement devices aimed at both sides of the rail web have been used. Strobe lights in combination with image sensing cameras having mirrors either on the rail web, the foot area of the rail, or even under the head area of the rail have been utilized. The rail centerline has been detected by the use of magnetic proximity sensors positioned near the web or head of the rail to sense flux density. Web centerline has been located mechanically by hand gauging with the use of mechanical feelers on the web of the rail.

U.S. Pat. No. 4,235,112 to Kaiser is also known and discloses laterally movable ultrasound transducers, one transmit-receive transducer and two receive transducers, which are automatically centerable on the rail while a rail fault detection device is moved along the rail. In this regard, a sensor head is movable laterally with respect to a carriage. The carriage moves along the rail longitudinally. The transducers in the sensor head are acoustically coupled to the rail and electrical signals, generated by the transducers based on reflected ultrasound energy, are used to generate a position error signal. A hydraulic position control mechanism, in response to the position error signal, controls the lateral movement of the transducers. The transducers are positioned laterally to null the error signal.

Several problems exist with prior approaches to detecting web centerline of a rail. Under many circumstances, the rail web, feet, or underside of the head, are not available to be probed by strobe lights; nor are they available for use with magnetic sensors, laser triangulation devices, nor mechanical feelers. For example, in many circumstances the rail web, feet, and in many cases, portions of the head are covered with high ballast or snow. In addition, road surfaces at road crossings are substantially level with the rail head and often cover the foot and web of the rail. As indicated, such conditions render many of the previously mentioned approaches ineffective. However, devices such as disclosed in U.S. Pat. No. 4,235,112 to Kaiser which utilize ultrasound through the head of the rail, are still capable of functioning to locate web centerline.

The Kaiser device as best understood, locates web centerline of a rail only when it is positioned as in FIG. 4, wherein the rail's web centerline is substantially perpendicular to the ground surface. The problem is that rail is normally canted as shown in FIG. 5, that is, the rails are canted inward at a cant angle $\theta$ with regard to a perpendicular to the ground surface. This cant angle $\theta$ is usually a predetermined angle created by the mounting of the rail upon the tie plate and can be intentionally varied in any stretch of rail, such as for curves.

Because of the cant angle, movement of a single ultrasound transmit-receive transducers and two receive transducers coupled to the head of a rail in a lateral direction, as described in U.S. Pat. No. 4,235,112, is not effective to detect the true web centerline of the rail. That is, web centerline with the Kaiser device can only be located if the web centerline is perpendicular to the ground surface, as shown in FIG. 4.

In addition to not being able to locate web centerline of a canted rail, none of these devices appear usable under many circumstances, as mentioned above, to determine rail cant, rail height, rail height loss, gauge face loss, and/or track gauge. These measurements can be very important for various aspects of maintenance of railway systems. Because of these many shortcomings of the prior art, the need for the present detection apparatus has arisen.

SUMMARY OF THE INVENTION

The apparatus of the present invention is capable of locating web centerline of a canted rail under various conditions, including a rail web covered by high ballast, snow, or road surfacing at road crossings. The apparatus includes an ultrasound sensor acoustically coupled to the head of the rail. The device transmits ultrasound pulses through the rail and generates electrical signals corresponding to received reflected ultrasound energy. Control circuitry responsive to the electrical signals generates control signals representative of a lateral and angular displacement of the ultrasound sensor with respect to the web centerline. The position of the ultrasound sensor with respect to the web centerline is adjusted as a function of the control signals.

In a preferred embodiment of the invention, the apparatus includes a carriage movable longitudinally along the rail. A cradle is supported from the carriage and separably movable in a lateral direction with respect to the longitudinal movement of the carriage and in an angular direction with respect to the lateral direction of the movement of the cradle. An ultrasound sensor is supported by the cradle and is acoustically coupled to the head of the rail for transmitting ultrasound energy through the rail and for generating electrical signals corresponding to reflected ultrasound energy therefrom. Control circuitry responsive to the electrical signals generates control signals representative of lateral and angular displacements of the ultrasound sensor with respect to the web centerline of the rail. The cradle and the ultrasound sensor supported thereby, are moved in lateral and angular directions in response to the control signals so that the ultrasound sensor continually seeks alignment with the rail web centerline.

The ultrasound sensor of the invention comprises a center transceiver and first and second transceivers positioned symmetrically on either side of the center transceiver. The transceivers are acoustically coupled to the head of the rail. Each of the transceivers transmits ultrasound energy through the head of the rail and generates electrical signals corresponding to received reflected energy from therein.

The control circuitry of the invention comprises circuitry for comparing electrical signals generated by the first ultrasound transceiver on one side of the center transceiver to the electrical signals generated by the second transceiver on the other side of the center transceiver. If the amplitudes of the electrical signals from the first and second side transceivers are approximately equal, then the center transceiver is positioned and oriented directly over and in line with the web centerline. Control signals representative of the lateral displacement of the center transceiver with respect to the web centerline are generated if the amplitude of the electrical signals from the center transceiver are greater than the amplitude of the electrical signals from either of the other transceivers. Control signals representative of the angular displacement of the center transceiver with respect to the web centerline are generated if the amplitude of the electrical signals from the center transceiver are less than the amplitude of the electrical signals from either of the other transceivers.

The invention further includes apparatus for measuring the lateral distance the center transceiver is moved in response to said control signals, and the angular rotation the center transceiver is moved in response to said control signals. Further, the apparatus determines the height of the rail as a function of the electrical signal generated by the center transducer when aligned with web centerline. From this height, rail height loss can be calculated. Gauge face wear for the rail can also be calculated.

BRIEF DESCRIPTION OF THE DRAWINGS

Thusly summarized, the present invention may be better understood, however, and the advantages made apparent to those skilled in the art by reference to the accompanying drawing wherein like reference numbers refer to like elements in the several figures and in which.

DETAILED DESCRIPTION OF THE INVENTION

In the following description of the invention, reference is made to the accompanying drawings which form a part hereof, and which show the preferred embodiment. It is to be understood, however, that other embodiments may be utilized and structural changes made without departing from the scope of the present invention.

Figure 1:
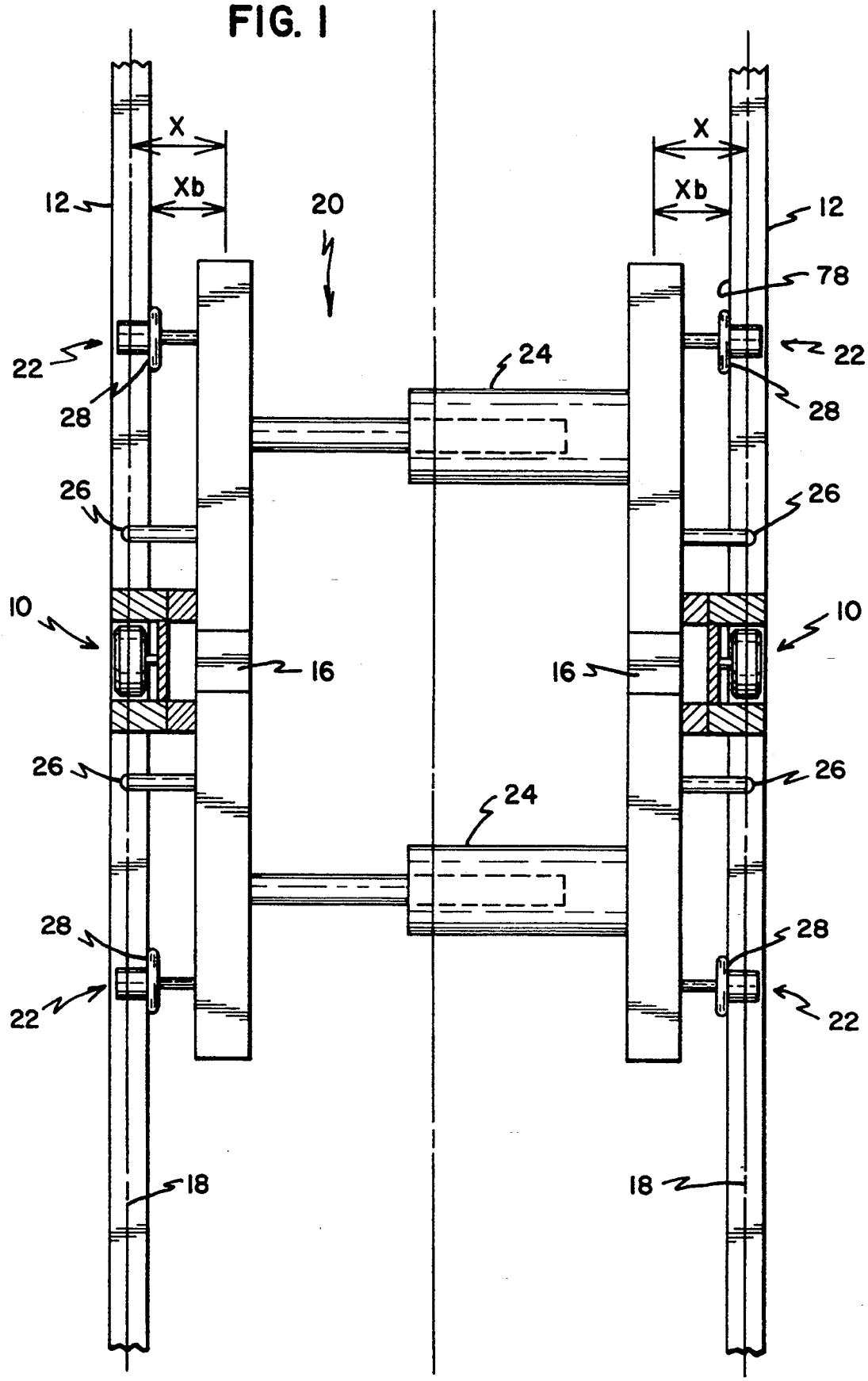
FIG. 1 is a top view of a carriage positioned on a pair of parallel rails with the detector of the present invention supported thereon.
Figure 2:
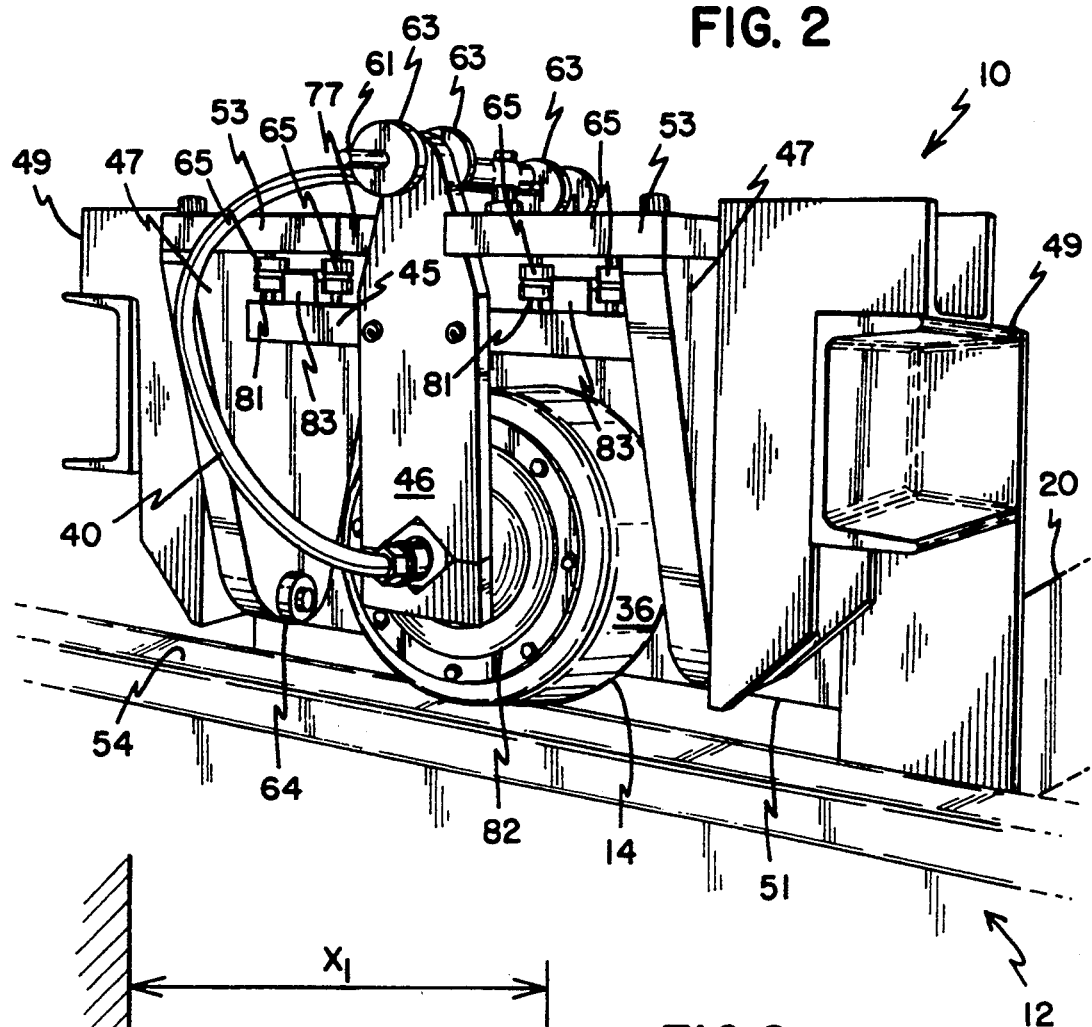
FIG. 2 is a perspective view of the cradle portion of the present invention supporting the ultrasound search wheel.
Figure 3:
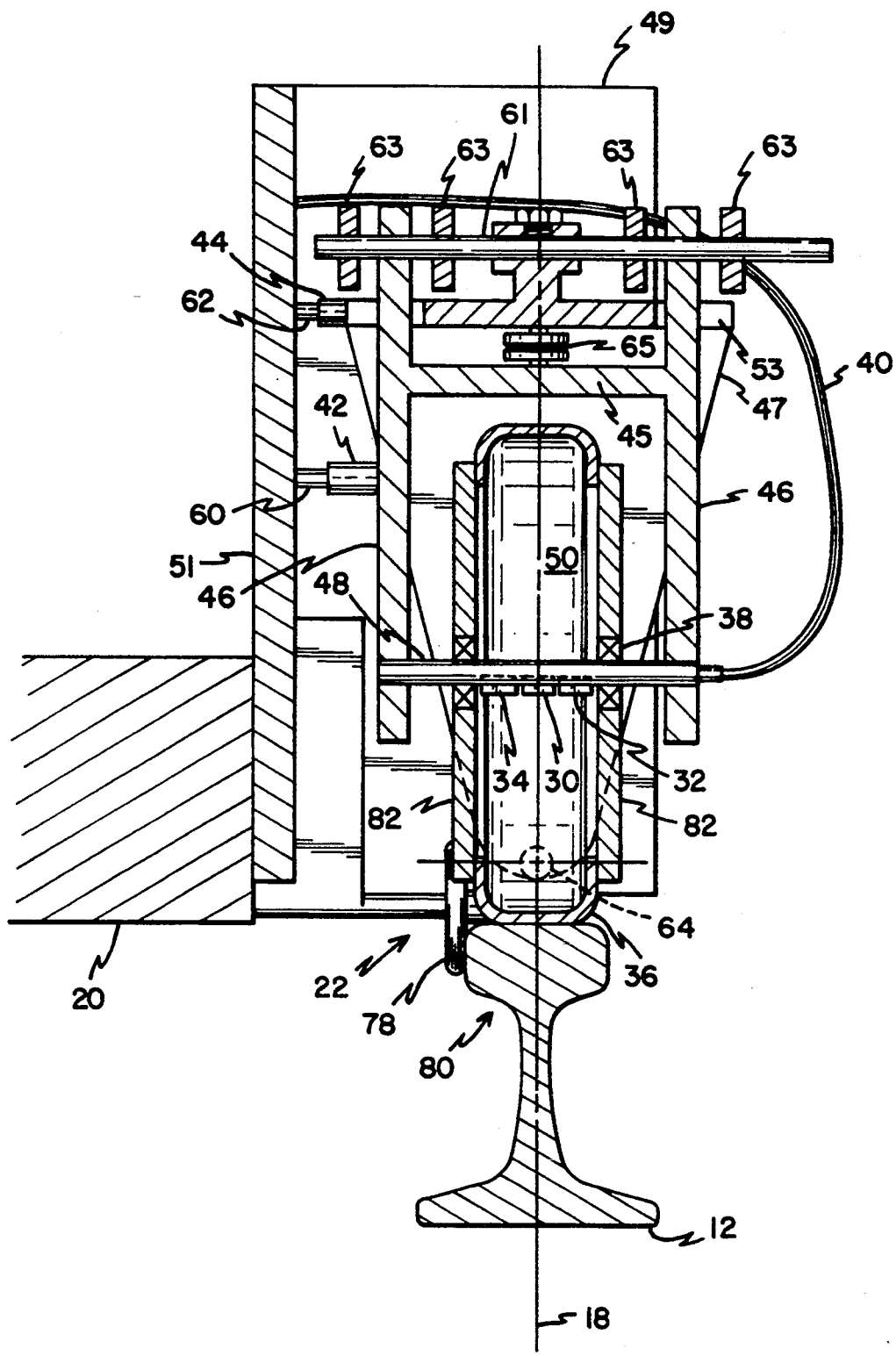
FIG. 3 is a cross-sectional view of the cradle of FIG. 2 coupled to the carriage and positioned on a rail.

With reference to FIGS. 1-3, the ultrasound rail web centerline detector of the present invention shall be described. Carriage 20 has coupled thereto a cradle 10 supporting an ultrasound roller search wheel or sensor 14 which is acoustically coupled to head surface 54 of rail 12. Head surface 54 is the top of the rail and defines generally a plane separating a first space thereabove and a second space therebeneath. The carriage 20, along with the cradle 10 supported thereby, is movable along the rail 12 in a longitudinal direction during the detection of web centerline of each rail. The web centerline determining mechanism includes the cradle 10 and roller search wheel 14 and is located in the first space above the plane to head surface 54, the second space being free of the mechanism.

The roller search wheel 14 within the cradle 10 is movable in a lateral direction by a jack, preferably hydraulic cylinder 42, with respect to a longitudinal plane established by the rail web centerline. In addition, the search wheel 14 is separably movable in an angular direction with respect to the lateral direction of movement, by another jack, preferably a hydraulic cylinder 44. The roller search wheel 14 includes ultrasound transceivers, 30, 32 and 34 for sensing the lateral and angular position of the roller search wheel with respect to the rail web centerline 18. The transceivers transmit ultrasound energy through the rail head surface 54 and generate signals corresponding to ultrasound energy reflected within said rail and received thereby. Control circuitry 16 receives the electrical signals from the transceivers 30, 32 and 34, generates, and applies control signals to the lateral adjustment hydraulic cylinder 42 and the angular adjustment hydraulic cylinder 44.

Linearly variable displacement transformers (LVDT's) 60 and 62 are operatively positioned on the hydraulic cylinders to measure the angular and lateral displacement of the search wheel 14 after adjustment is made to provide a closed loop mechanism for adjusting the roller search wheel 14 in accordance with the control signals generated by the control circuitry 16. The angular displacement is directly translatable from linear measurement by the LVDT. Thus, the roller search wheel 14 is continuously positioned directly over the rail web centerline 18 as the carriage 20 is moved longitudinally along the rail 12. The jacks used in the system and the measurement devices for measuring the lateral and angular displacement can also be pneumatic devices with displacement measurement by LVDT's, electric linear actuators with built in potentiometers for measuring the displacement or any other combination of devices which would operatively close the loop to provide accurate adjustment.

The distance (X), FIG. 1, of the rail web centerline from a reference point on the carriage 20 is determined from the displacement measured by the LVDT's, 60 and 62. This measurement, together with measurement of the height of the rail from the amplitude of the reflected energy received by the center transceiver 30, provide data necessary for calculating various other characteristics of the rail 12 useful in maintenance thereof. In this regard, the rail web centerline 18 is located and other rail characteristics are obtained for such purposes as positioning a grinding machine for proper grinding of the rail.

Referring now to all the figures, FIG. 1–8, the rail web centerline detection apparatus shall be described in further detail. Referring first to FIG. 1, carriage 20 is shown coupled to rails 12 by the wheels 22 thereof. With respect to each rail, flanges 28 are forced in contact with gauge face 78 of the rail head 80 by bias jacks 24. In this manner, the wheel flange 28 of each of the wheels 22 is forced into continuous contact with the gauge face 78 by the bias jacks 24 and independent of the amount of gauge face loss or wear of the rail system. As such, the system is self correcting for gauge face loss. In addition, by measuring the distance between the members biased by jacks 24, such as by an LVDT, the gauge of the rail can be determined with the use of the predetermined distance $X_b$, FIG. 1.

Cradles 10 are supported by carriage 20; one on each side of the carriage 20 between a pair of wheels 22. A fluid outlet 26 is positioned forward and rearward of each cradle to apply fluid to the rail for acoustic coupling between the roller search wheel 14 (FIG. 3) and rail head 80. The fluid outlets 26 are positioned to provide acoustic coupling whether the carriage is moving in the forward or rearward direction.

Cradle 10 is shown in further detail in FIGS. 2 and 3. Cradle 10 is coupled to carriage 20 by cradle supports 49. Cradle supports 49 are connected together by frame 51. Each of cradle supports 49 includes an angular pivot 64 which couples the cradle supports 49 to angular movement support members 47 and allows for angular displacement of search wheel 14 with respect to rail 12. Angular support members 47 along with members 53 which extend transverse to the angular support members 47, form a channel 77 for movement of lateral movement supports 46 therethrough. Coupling rollers 65 allow for movement of the search wheel 14 in a lateral direction to rail 12. Coupling rollers 65 have a first portion 81 attached to members 53 and a second portion 83 attached to plate 45, providing a coupling of angular movement support members 47. Plate 45 connects lateral movement support members 46 with hollow axle 48 therebetween. Bar 61 connected between lateral movement support members has stops 63 positioned thereon to prevent excessive lateral movement.

Hollow axle 48 extends through roller search wheel 14 and is affixed to the angular movement support members 47. Bearings 38 support search wheel 14 relative to axle 48. Three ultrasound transceivers are positioned on the precision machined axle 48 within the roller search wheel 14. Center transceiver 30 is centered on the axle 48. Gauge transceiver 34 is positioned on the gauge side of the rail a predetermined distance from the center transceiver 30, and field transceiver 32 is positioned on the field side of the rail the same predetermined distance from the center transceiver 30 as gauge transceiver 34 is from center transceiver 30.

The search wheel sides 82 are connected by a flexible material 36 which is slightly compressed when positioned on rail head 80- Within the wheel, fluid 50 is utilized for acoustic coupling of the transceivers to the rail 12 and for preventing turbulence therein. Although all three transceivers are shown positioned in the same search wheel, it is understood that alternatively several search wheels could be utilized.

Search wheel 14 is movable in the lateral direction by lateral adjustment hydraulic cylinder 42 as lateral support members 46 slide through channel 77 via coupling rollers 65. Search wheel 14 is movable in the angular direction per pivot 64 by angular adjustment hydraulic cylinder 44. LVDT 60 is positioned on lateral adjustment hydraulic cylinder 42 and measures the lateral displacement of the search wheel 14 with respect to carriage 20. Angular adjustment hydraulics 44 has an LVDT 62 positioned thereon for measuring the angular displacement of search wheel 14 with respect to vertical.

Figure 4:
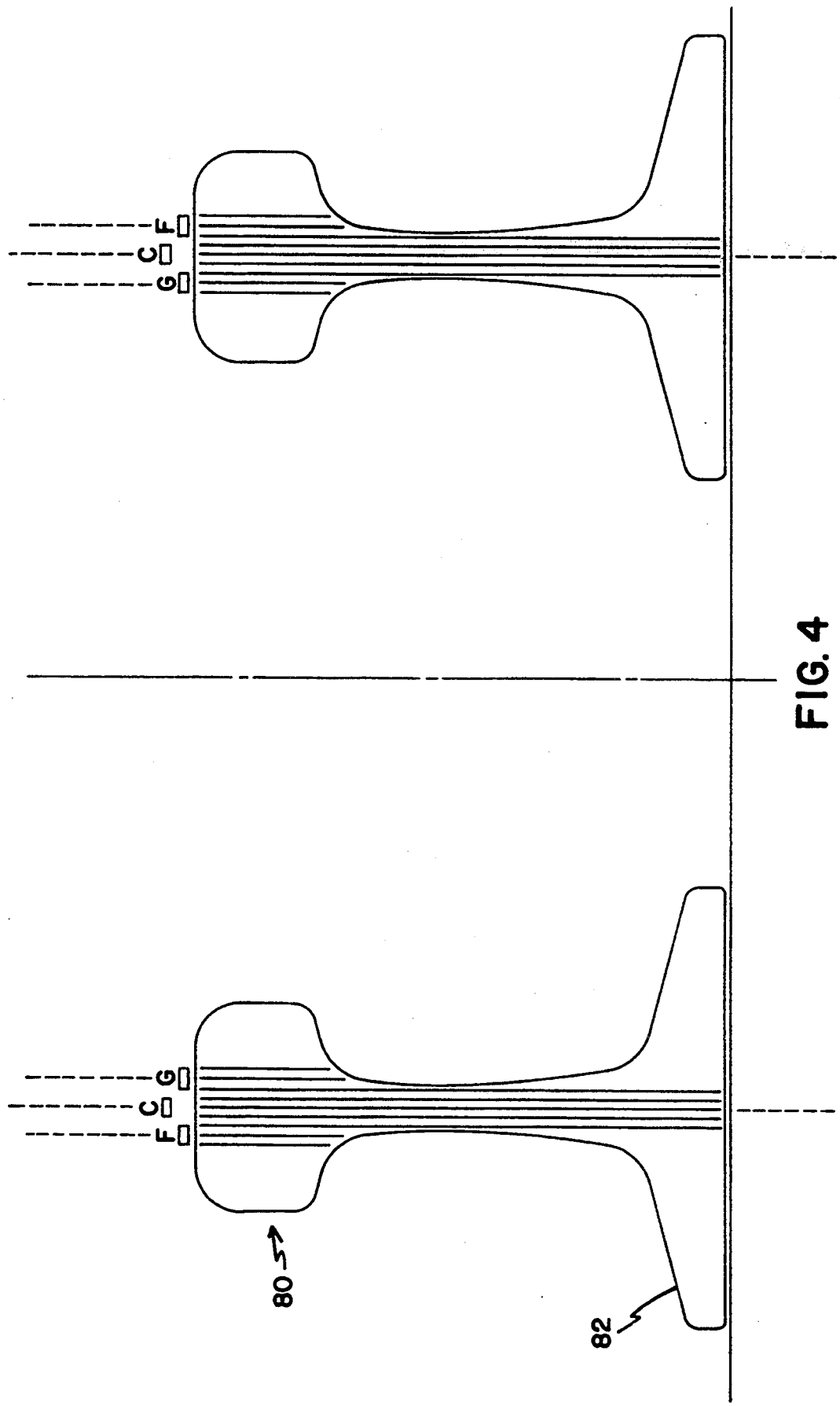
FIG. 4 schematically represents the present invention utilizing ultrasound through the head of a rail having a web centerline perpendicular to the ground surface.
Figure 5:
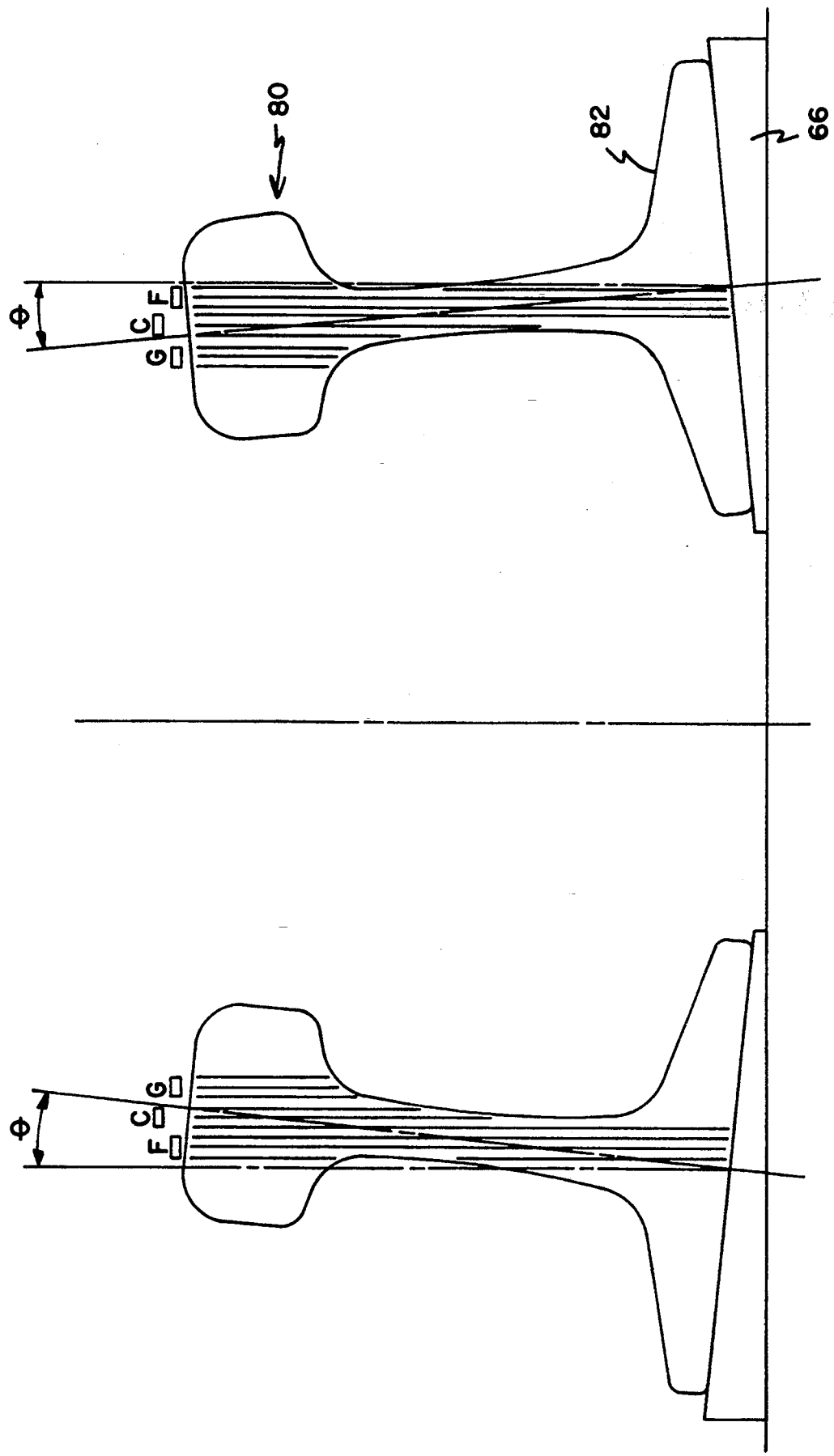
FIG. 5 schematically illustrates the use of the present invention with a canted rail.
Figure 6:
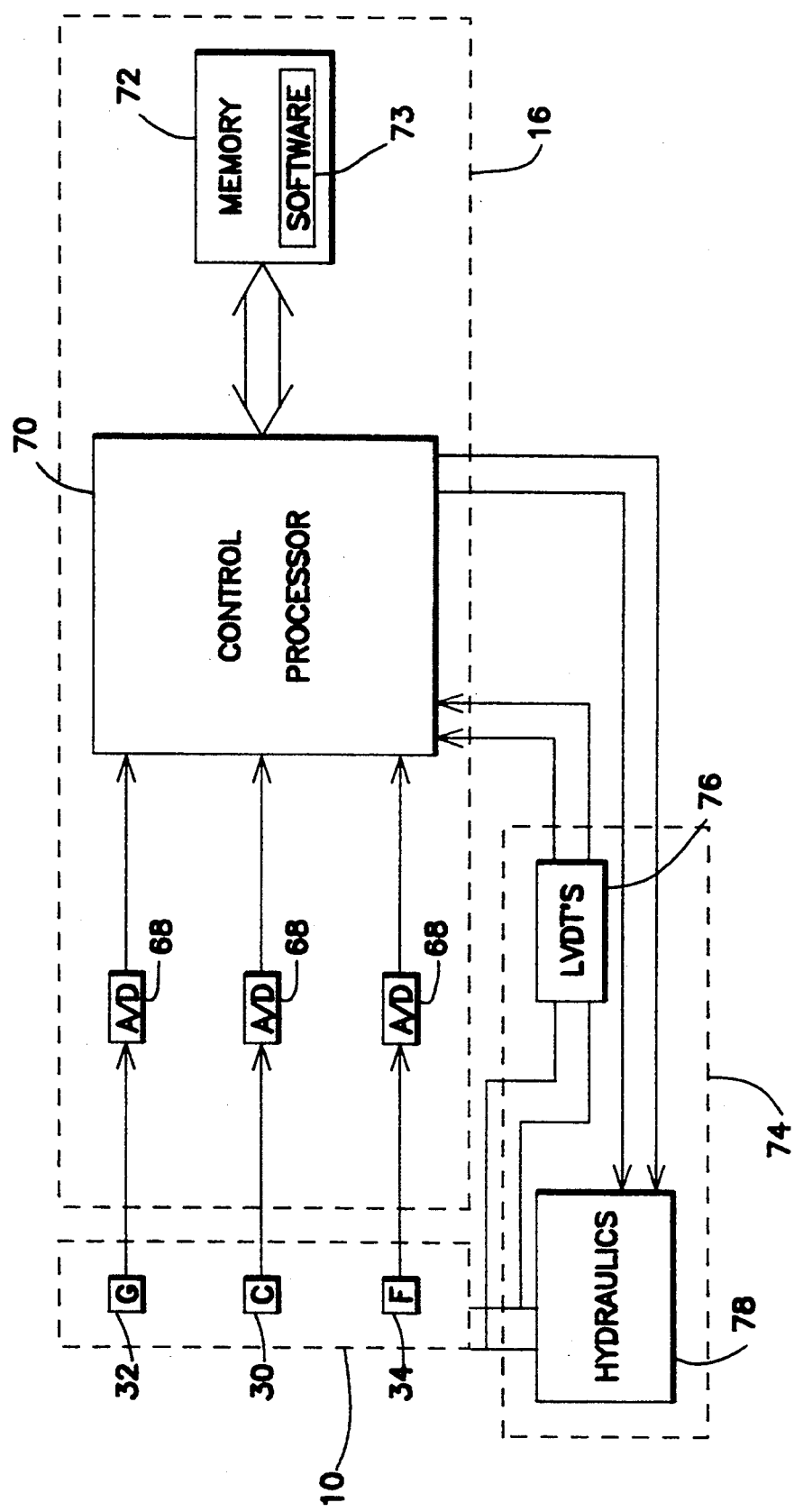
FIG. 6 is a schematic block diagram of the ultrasound rail web centerline detector of the present invention.

As wheel 14 is rolled along rail 12, transceivers 30, 32, and 34, when energized, simultaneously transmit ultrasound signals into the rail head 80. All three transceivers receive echoes from within the rail 12 and transduce the echoes or energy into electrical signals. After the echoes are converted to electrical signals the transceivers may once again transmit ultrasound signals. These electrical signals are applied to control circuitry 16 via the electrical lines 40 flowing out of the hollow axle 48- As shown in FIG. 4 and 5, each transceiver's ultrasound signals are represented by three lines extending from each transceiver.

Referring now to FIGS. 4, 5, 6, and 7, the operation of the web centerline detection device will be described. The roller search wheel 14 is positioned on the rail 12 and the system is calibrated. Calibration is performed by adjusting the search wheel position until the center transceiver 30 is directly over and in line with the web centerline 18 of the rail 12. As discussed further below, the center transceiver 30 is directly over and in line with the rail web centerline 18 when signals generated by the field and gauge transceivers 32, 34 are approximately equal in amplitude, within error parameters, as would be the case for the rail on the right side of FIG. 4. The error parameters define the accuracy of web centerline measurements.

After calibration of the system, baseline parameters for the calibrated position are stored. The baseline parameters include $X_B$, the position of rail centerline from a reference point on carriage 20 when calibrated, and cant angle $\theta$, an angle relative to vertical directly the result of how the rail is positioned on tie plate 66 at calibration. For example, foot 82 of rail 12 is raised on the field side of the rail a predetermined distance above the position of the foot 82 on the gauge side of the rail 12. These baseline parameters are determined by use of the LVDT's positioned on the hydraulic cylinders which provide movement of the search wheel, both laterally and angularly.

In addition, reference data is stored in memory 72 of control circuitry 16. The reference data includes the initial height of the rail 12 when the rail was first laid, and the parameter $X_b$, a fixed distance from the carriage reference point to the wheel flange 28 which is against the gauge face 78.

After calibration and upon movement of the carriage 20 longitudinally along rail 12, all three transceivers (field transceiver 34, center transceiver 30, and gauge transceiver 32) are fired simultaneously, transmitting ultrasound energy through rail head 80 into rail 12. Reflected energy or echoes received by each transceiver from the base of the rail or from other portions of the rail, such as the lower portion of the rail head, are converted into electrical signals (signals produced thereby are hereinafter referred to as transceiver signals F, C, and G respectively) and applied to analog to digital (A/D) converters 68. A/D converters 68 digitize the analog signals from the transceivers representative of the amplitude of the signals from each transceiver.

Control processor 70 receives the digitized signals and under control of software 73 compares the amplitude of digitized signal F with digitized signal G. The digitized signals from transceivers F and G have an approximately equal amplitude when the roller search wheel is directly over and in line with the rail web centerline, as can be seen by the right rail of FIG. 4, wherein the three lines representative of the ultrasound energy for the F and G transceiver are approximately equal. If such is the case, signals representative of the amplitude of signal C and the measurements of X and $\theta$ as reflected by the displacement of LVDT's with respect to the baseline parameter 70 are received by the control circuitry 16. From this information as will be described below various characteristics of the rail are calculated.

If however, the signal F of the field transceiver 34 and the signal G of the gauge transceiver 32 are not equal, or within the error parameters, then the larger of the digitized signals F and G is compared with the digitized signal C of center transceiver 30. With specific reference to the left rail in FIG. 5, such a comparison will be further described. If signal F is greater than signal G, which is shown by the three lines extending from transceiver F being greater than the three lines extending from transceiver G, then signal C is compared with signal F. As is shown in FIG. 5, signal F is greater than signal C. The difference in amplitude of these signals is proportional to the amount of cant offset from the baseline cant angle $\theta$. A control signal representative of the amount of offset is used to adjust the cant per the closed loop adjustment hydraulics 74.

The closed loop adjustment hydraulics 74 include lateral adjustment hydraulic cylinder 42 and angular adjustment hydraulic cylinder 44. These hydraulic cylinders are activated in a closed loop with LVDT's 60 and 62. The LVDT's 60, 62 provide the means for determining when lateral or cant adjustment has been accomplished. As indicated previously, any combination of devices which would operatively close the loop to provide adjustment can be utilized for the adjustment hydraulics and LVDT's.

If signal C is greater than signal F then the cant angle does not need to be adjusted. However, the center transceiver 30 is not positioned directly over the web centerline 18. Therefore, lateral adjustment needs to be performed. The amplitude difference between G and F is proportional to the amount of lateral offset from the baseline $X_B$. A control signal representative of the required lateral adjustment is then generated and applied to the closed loop adjustment hydraulics 74 for laterally moving the search wheel 14.

Figure 7:
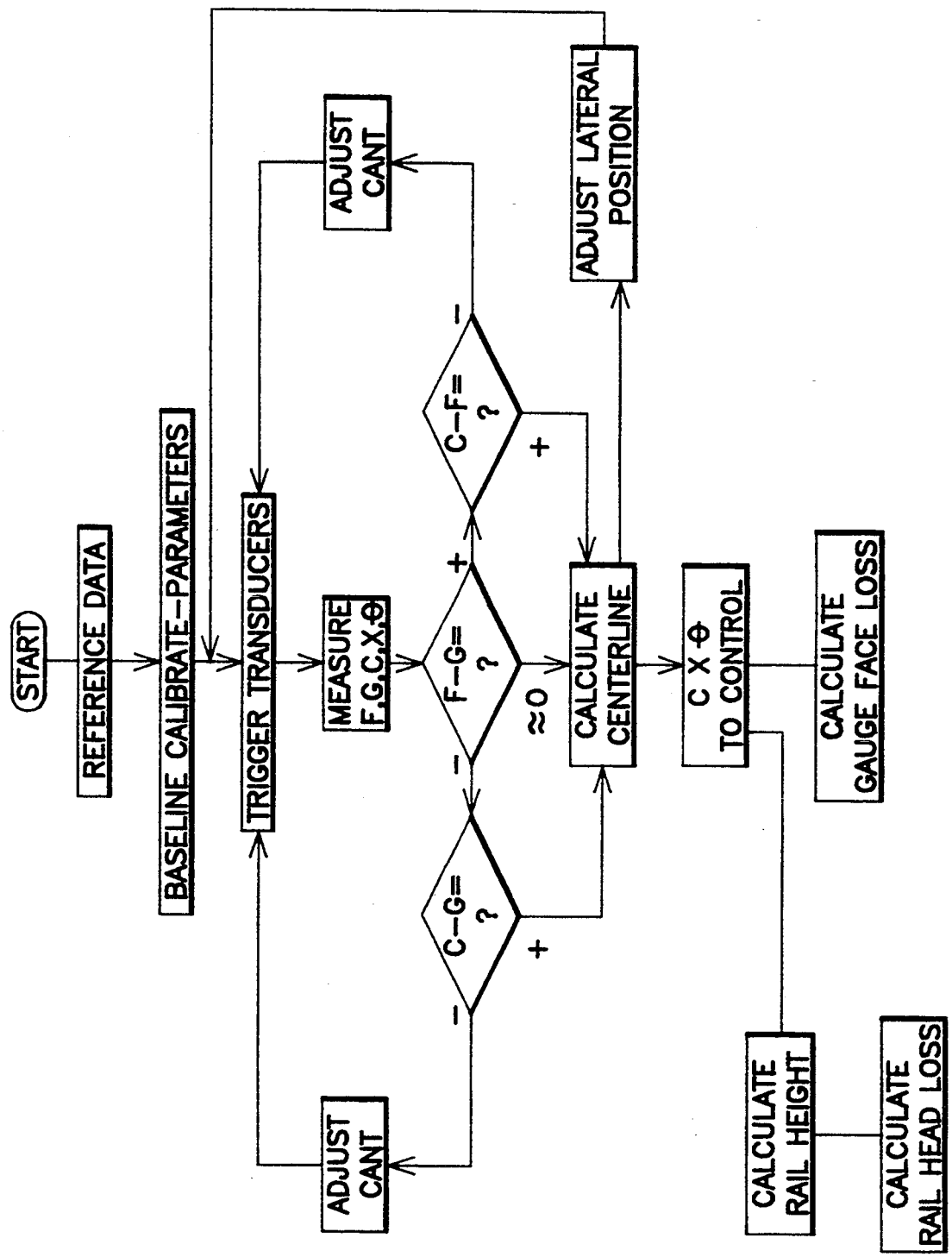
FIG. 7 is a block diagram illustrating the operation of the apparatus of the present invention.

Similar comparisons are made if signal F is less than that of signal G as shown in FIG. 7. Once the lateral and cant adjustments is made, F are approximately equal to G and the parameters C, X, and $\theta$ are utilized for maintenance tasks. These parameters are measured continuously as the carriage 20 is moved longitudinally along the rail 12, approximately three times per second.

Figure 8:
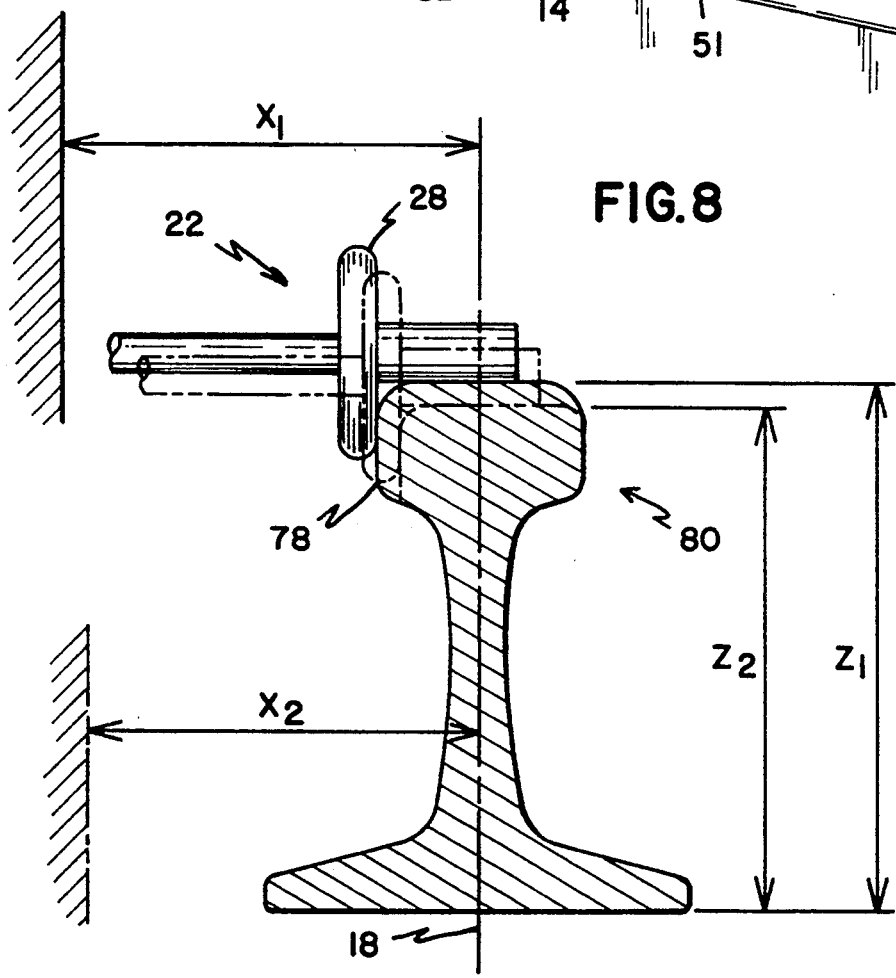
FIG. 8 illustrates measurements which can be calculated with respect to the rail with use of the present invention.

With reference to FIG. 8, several characteristics of a rail are illustrated. With respect to measured parameters, rail height is directly translatable from the amplitude of signal C when the center transceiver 30 is directly over and in line with web centerline 18. By comparing the initial reference height of the rail $Z_1$, with the actual height of the rail $Z_2$, rail height loss from wear of the rail can be determined. Likewise, by comparing the initial value of X when the rail is first laid, $X_1$, with the actual value, $X_2$, gauge face loss can be determined. Also, by taking the difference between the actual value, $X_2$, and the fixed dimension from carriage 20 to wheel flange 28, $X_b$, the dimension from centerline to gauge face is determined. When this dimension is compared to the initial gauge face from centerline dimension when the rail is first laid, gauge face loss is established. Thus, the present invention can be used to obtain relevant characteristics of a track, which can then be used for use decisions and various maintenance operations.

Although the present invention has been described above in a preferred form, those skilled in the art will readily appreciate that various modifications can be made to it without departing from the spirit and scope of the invention as bounded by the claims of the application itself. In particular, the web centerline detection device is recognized as capable of being used to locate the web centerlines of beams and shapes used in other industries.

What is claimed is:

1. An apparatus for locating a web centerline of a longitudinal member having a head, a base, and a web therebetween, comprising:
    a plurality of ultrasound means, including a center transceiver and a first and second side transceivers fixedly positioned symmetrically on opposite sides of said center transceiver, adapted for acoustical coupling to either the head or the base of said member for transmitting and receiving ultrasound energy through said member and for generating electrical signals corresponding to received reflected ultrasound energy, each of said ultrasound means transmitting and receiving ultrasound energy through said member and generating discrete electrical signals for each of said ultrasound means;
    control means responsive to mutual relative strengths of said electrical discrete signals for generating control signals indicating a lateral displacement and a angular displacement of said ultrasound means from said web centerline; and
    means for adjusting the position of said ultrasound means relative to said web centerline as a function of said control signals,
    said control means comprising:
    first means for comparing the electrical signals generated by said first side transceiver to the electrical signals generated by said second side transceiver whereby approximately equal amplitudes of the electrical signals generated by said first and said second transceiver indicate that the center transceiver is aligned directly with said web centerline;
    first means for generating control signals representative of the lateral displacement of the plurality of ultrasound means from the web centerline as a function of the electrical signals generated from the center and side transceivers if the amplitudes of the electrical signals from said center transceiver are greater than the amplitudes of the electrical signals from either of the side transceivers; and
    second means for generating control signals representative of the angular displacement of said plurality of ultrasound means from the web centerline as a function of the electrical signals generated from the center and side transceivers if the amplitudes of the electrical signals from the center transceiver are less than the amplitudes of the electrical signals from either of the side transceivers.

2. An apparatus for locating a web centerline of a rail having a head and a web comprising:
    a carriage movable longitudinally along the rail;

a cradle supported from said carriage and separably movable in a lateral direction with respect to the longtiudinal movement of said carriage and in an angular direction with respect to said lateral direction of movement of said cradle;

a plurality of ultrasound means supported by said cradle and adapted for acoustical coupling to said head of the rail for transmitting and receiving ultrasound energy through said rail and for generating electrical signals corresponding to received reflected ultrasound energy, said ultrasound means including a center transceiver and first and second side transceivers fixedly positioned symmetrically on opposite sides of said center transceiver at positions relative to the web of said rail, each of said transceivers transmitting and receiving ultrasound energy through said rail and generating electrical signals corresponding to received reflected ultrasound energy, each of said ultrasound means transmitting and receiving ultrasound energy through the rail and generating discrete electrical signals for each of said ultrasound means;

control means responsive to mutual relative strengths of said discrete electrical signals for generating control signals representative of the lateral and the angular displacements of the ultrasound means from the web centerline of the rail;

first means responsive to said control signals for moving said cradle and said plurality of ultrasound means supported thereby in the lateral direction so that said plurality of ultrasound means is laterally aligned with the web centerline of said rail; and second means for moving said cradle and said plurality of ultrasound means supported thereby in the angular direction so that said plurality of ultrasound means is angularly aligned with the web centerline of said rail, and said control means comprising:

first means for comparing the electrical signals generated by said first side transceiver to the electrical signals generated by said second side transceiver whereby approximately equal amplitudes of the electrical signals generated by said first and said second transceiver indicate that the center transceiver is aligned directly with said web centerline;

second means for comparing the electrical signals generated by said center transceiver with the electrical signals generated by said first side transceiver and with the electrical signals generated by said second side transceiver;

first means for generating control signals representative of the lateral displacement of the center transceiver from said web centerline as a function of the electrical signals generated from the center transceiver and the side transceivers if the amplitude of the electrical signals from the center transceiver is greater than the amplitude of electrical signals from either of the side transceivers; and second means for generating control signals representative of the angular displacement of the center transceiver from the web centerline as a function of the electrical signals generated from the center and side transceivers if the amplitudes of the electrical signals from the center transceiver are less than the amplitude of the electrical signals from either of the side transceivers.

3. A method for locating web centerline of a rail having a head, a base and web, comprising the steps of:

acoustically coupling a center ultrasound transceiver and two side ultrasound transceivers to the head of the rail, said side ultrasound transceivers being positioned symmetrically on opposite sides of said center transceiver;

transmitting ultrasound energy through the head of said rail;

generating transceiver signals as a function of reflected ultrasound energy received by said center and side transceivers;

generating control signals indicating a lateral displacement and an angular displacement of said center transceiver from the web centerline as a function of the generated transceiver signals; said control signals generation further including the steps of:

comparing the transceiver signals generated by one of said side transceivers to the transceiver signals generated by said other of said side transceivers so that if the amplitudes of the transceiver signals are approximately equal then the center transceiver is positioned directly over said web centerline; and if said signals from said side transceivers are not equal, then comparing the electrical signals generated by one of said side transceiver with the signals generated by said center transceiver;

if the amplitude of the electrical signals from said center transceiver are greater than the amplitude of the electrical signals from one of said side transceivers, then generating control signals indicating the angular and lateral displacement of the center transceiver with respect to the web centerline; and if the electrical signals from said center transceiver are less than the electrical signals from one of said side transceiver, then generating control signals indicating the angular and lateral displacement of the center transceiver with respect to the web centerline;

adjusting the lateral and angular position of the acoustically coupled transceivers in response to said control signals such that said center transceiver is directly aligned over said web centerline and such that ultrasound energy transmitted through said head is parallel to said web centerline; and moving the acoustically coupled transceivers longitudinally along the rail.

4. A method according to claim 3 wherein said adjusting step comprises the steps of:

measuring the position of said center transceiver from a reference point on said carriage and generating a signal indicating said position;

comparing said position signal with the control signals indicating said lateral displacement and said angular displacement of said center transceiver from said web centerline and generating adjusting signals as a function thereof; and employing said adjustment signals to adjust said center transceiver and said other transceivers accordingly.

5. A method according to claim 4 further comprising the steps of:

calculating the height of said rail as a function of said transceiver signal generated by said center transceiver when said center transceiver is positioned directly over said web centerline; and comparing said calculated height to a predetermined reference height to determine rail height loss.

6. A method according to claim 4 further comprising the steps of:

calculating the distance between said reference point and said center transceiver when positioned directly over said web centerline; and comparing said calculated distance to a predetermined reference distance to determine gauge face loss.

* * * * *